United States Patent [19]
Lai

[11] Patent Number: 5,358,703
[45] Date of Patent: Oct. 25, 1994

[54] METHOD FOR THE DETECTION OF NITRIC OXIDE

[75] Inventor: Ching-San Lai, Brookfield, Wis.

[73] Assignee: MCW Research Foundation, Inc., Milwaukee, Wis.

[21] Appl. No.: 127,665

[22] Filed: Sep. 27, 1993

[51] Int. Cl.$^5$ .................. A61K 49/00; G01N 33/00
[52] U.S. Cl. ............................. 424/9; 436/118; 436/173
[58] Field of Search ............ 436/116, 118, 173; 324/300, 316; 514/2, 21; 530/350; 424/10, 9

[56] References Cited

U.S. PATENT DOCUMENTS

| | | | |
|---|---|---|---|
| 4,954,526 | 9/1990 | Keefer | 514/611 |
| 5,035,878 | 7/1991 | Borch et al. | 424/10 |
| 5,059,712 | 10/1991 | Griffith | 562/560 |
| 5,094,815 | 3/1992 | Conboy et al. | 422/52 |
| 5,132,453 | 7/1992 | Griffith | 562/560 |
| 5,169,765 | 12/1991 | Borch et al. | 435/70.4 |
| 5,187,193 | 2/1993 | Borch et al. | 514/476 |

OTHER PUBLICATIONS

"On-line detection of nitric oxide . . . paramagnetic resonance spectroscopy", Mordnintcev et al., Anal Biochem, 1990, 142-6.

"Potentiation of nitric oxide . . . spin trapping", Tuminaga et al., Brain Research 614 (1993) 342-346.

"In vivo Spin Trapping of Nitric Oxide in Mice", Komarov et al., Biochem and Biophysic Research Comm, 1191-1198.

"Protective and Pathological Roles of Nitrix Oxide in Endotoxin Shock", Cardiovascular Research, 1992, vol. 26, pp. 48-57.

Kelm, M., and Schrader, J. (1990) Circ. Res., 66:1561-1575.

Green, L. C., Wagner, D. A., Glogowski, J., Skipper, P. L., Wishnok, J. S., and Tennenbaum, S. R. (1982) Anal. Biochem., 126:131-138.

Bartholomew, B. (1984) Fd. Chem. Toxic., 22:541-543.

Shinobu, L. A., Jones, S. G., and Jones, M. M. (1984) Acta Pharmacol, et Toxicol., 54:189-194.

Yamamoto, H. A. (1992) Fd. Chem. Toxic., 30:887-890.

*Primary Examiner*—Nina Bhat
*Attorney, Agent, or Firm*—Quarles & Brady

[57] ABSTRACT

A method of detecting nitric oxide in an aqueous body fluid of a mammal comprises introducing into the body fluid the agents required to form a water-soluble, stable, paramagnetic complex with nitric oxide and then subjecting the body fluid to magnetic resonance methods which can detect the complex to determine if any nitric oxide was present. A paramagnetic complex containing nitric oxide also is described, as well as, a method of diagnosing septic shock in a mammal by stabilizing and detecting the presence of nitric oxide in a body fluid of the mammal.

6 Claims, 8 Drawing Sheets

METHOD FOR THE DETECTION OF NITRIC OXIDE

FIELD OF THE INVENTION

The present invention relates to the detection of nitric oxide. More particularly, it relates to methods of detecting nitric oxide in the body fluids of a mammal and novel complexes containing nitric oxide that are useful in a method for determining if a mammal has septic shock,

BACKGROUND OF THE INVENTION

It is known that nitric oxide is formed enzymatically in vivo from arginine as a normal metabolite which is an important component of endothelium-derived relaxing factors (EDRFs). The EDRFs are believed to participate in regulation of blood flow and vascular resistance. In addition to vascular endothelium, macrophages have also been shown to produce nitric oxide in the body which is a component of their cell killing and/or cytostatic function.

The enzyme which forms nitric oxide from arginine, i.e., nitric oxide synthase, is believed to occur in two distinct isoforms, namely the constitutive isoform and the inducible isoform.

The constitutive isoform is present in normal endothelial cells, neurons and some other tissues. The formation of nitric oxide by the constitutive isoform in endothelial cells is thought to play a role in normal blood pressure regulation.

The inducible isoform of nitric oxide synthase has been isolated from activated macrophages and is induced by various cytokines or combinations of cytokines in endothelial cells and vascular smooth muscle cells. It is believed that in septic shock or cytokine-induced shock that the observed life-threatening hypotension is due mainly or wholly to production of larger than normal amounts of nitric oxide by the inducible isoform of nitric oxide synthase.

Septic shock is an acute and serious cardiovascular collapse resulting from the systemic response to a bacterial infection, and is manifested by hypotension, a reduced response to vasoconstrictors, generalized tissue damage and multi-organ failure. It is the most common cause of death in the intensive-care unit; 400,000 cases of septicemia per year in the United States with mortality rates between 25% and 50%. The steadily increasing incidence of septic shock stems from an increasing proportion of elderly in the population, increasing frequency of invasive surgical procedures, extensive use of immunosuppressive and chemotherapeutic agents, and increasing prevalence of chronic debilitating conditions. Because the mechanisms underlying sepsis and septic shock are not yet known, therapeutic interventions have been largely ineffective.

A common cause of septic shock is Gram-negative bacterial infection. The lipopolysaccharide (LPS), an integral part of the outer layer of the Gram-negative bacterial cell wall, is instrumental in bringing about septic shock. Upon lysis of the bacteria, LPS is released into the surrounding medium, forming a micelle-like solute, known as endotoxin. Intravenous administration of LPS in animals and man produces a shock-like syndrome. Despite extensive studies, the reasons for the vascular effects of endotoxaemia are not clear, which have been attributed to increasing circulating levels of vasoactive angiotensin II and catecholamines, bradykinin, platelet activating factor, prostaglandins and leukotrienes, thromboxane A2, endothelin, phospholipase $A_2$, and more recently, to the cytokines such as interleukin-1 (IL-1), IL-6, IL-8, tumor necrosis factor, and interferon-$\gamma$. An interplay between these vasoconstrictors and vasodilators has been presumed to be the reason for the complex cardiovascular profile in endotoxin shock.

At present, diagnosis of septic shock involves monitoring the following clinical manifestations: (a) a body temperature greater than 38° C. or less than 36° C., (b) a heart rate greater than 90 beats per minute, and (c) a breath rate greater than 20 breaths per minute, and (d) an alteration in the white blood cell count greater than $12,000/mm^3$ or less than $4,000/mm^3$. The poor prognosis is, due at least in part to, the lack of reliable diagnostic tools to identify patients at greatest risk.

The relatively recent identification of nitric oxide as a signal transmitter in mediation of blood pressure regulation, neurotransmission, and macrophage-induced cytotoxicity and cytostasis has generated tremendous research interest. To understand the mechanisms by which nitric oxide, a diffusible free radical with a lifetime of a few seconds mediates various physiological and pathophysiological processes, it is necessary to have a method of detecting nitric oxide in real time near its sites of production and action. Several nitric oxide detection methods have been developed. These include chemiluminescence assay, oxyhemoglobin assay, GC-MS detection, and nitrosyl-hemoglobin formations detected by electron paramagnetic resonance (EPR) spectroscopy at liquid nitrogen temperatures. In addition, the production of nitric oxide can also be indirectly detected by measuring its end products $NO_2^-$/$NO_3^-$. However, none of these techniques in their present forms can be used for real time detection of nitric oxide in vivo or in the isolated body fluids.

As a result, there is a need for a method of detecting nitric oxide in real time in vivo or in isolated body fluids. In addition, because it is so often lethal, there also is a need for a fast and easy method of determining if a patient has septic shock.

BRIEF SUMMARY OF THE INVENTION

It is an object of the present invention to disclose a method of detecting nitric oxide in real time in body fluids.

It also is an object to disclose a fast and easy method of determining if a patient has septic shock by determining if the patient's body fluid(s) contain an abnormally high amount of nitric oxide.

It is further an object to disclose novel paramagnetic complexes containing nitric oxide which can be formed in a body fluid of a mammal and detected by non-invasive magnetic resonance methods.

The method of the present invention for detecting nitric oxide in real time in an aqueous body fluid comprises forming with any nitric oxide in the body fluid a water-soluble paramagnetic complex which has a lifetime of about 30 minutes and can be detected by magnetic resonance, such as electron paramagnetic resonance (EPR) spectroscopy or magnetic resonance imaging (MRI).

The method of the present invention for determining if a patient has septic shock comprises introducing into an aqueous body fluid of the patient a safe and effective amount of a chelating agent or preferably a metal-chelator which forms a water-soluble, paramagnetic complex with the excess nitric oxide which is present in the body fluid of a patient having septic shock and then subjecting the body fluid to non-invasive detection to see if the complex is present and the patient has septic shock.

The novel water-soluble, stable, paramagnetic complex of the present invention is the complex which is formed with nitric oxide when a metal-chelator, preferably consisting of N-methyl-D-glucamine dithiocarbamate (MGD) and reduced iron ($Fe^{2+}$), is formed in or added to a body fluid containing nitric oxide (.NO).

It will be apparent to those skilled in the art that in addition to the above objects, other advantages may be obtained by the practice of the present invention.

DESCRIPTION OF THE PREFERRED EMBODIMENT

In the preferred method of the invention, nitric oxide which has a lifetime of a few seconds in an aqueous solution, such as a body fluid, is trapped and stabilized for up to 30 minutes by injecting a metal-chelator, preferably consisting of N-methyl-D-glucamine dithiocarbamate (MGD) and reduced iron ($Fe^{2+}$), intravenously into a body fluid of a mammal to form a stable and water-soluble paramagnetic complex [$(MGD)_2$—$Fe^{2+}$—NO]. This complex, which gives rise to a three-line spectrum characteristic of mononitrosyl-$Fe^{2+}$ complexes, can be detected by a non-invasive magnetic resonance method, such as a spin-trapping technique using EPR spectroscopy at ambient temperatures.

We have used this spin-trapping technique in combination of S-band (3.5 $GH_z$) EPR spectroscopy to detect the in vivo release of nitric oxide (.NO) from sodium nitroprusside (SNP) in the blood circulation of mice. SNP, or $Na_2[Fe(CN)_5NO]$, has been used clinically in the treatment of severe hypertension and myocardial infarction. Its vasodilating effect is attributed to releasing .NO which activates guanylate cyclase (EC 4.6.1.2).

As a result we have been able to demonstrate the real time in vivo release of .NO from SNP.

By use of the method of the present invention we also have been able to detect nitric oxide production in vivo in mammals, such as mice, having septic shock.

The practice of the invention is further illustrated by the Examples:

EXAMPLE 1

In Vivo Detection of Nitric Oxide

MATERIALS AND METHODS

ICR mice (female, 20–30 g) were supplied by Harlan Sprague Dawley (Indianapolis, Ind.). Sodium nitroprusside, α-ketoglutarate, sodium thiosulfate and tris(hydroxymethyl)aminomethane (Tris) were obtained from Sigma (St. Louis, Mo.). Sodium pentobartital was from Anpro Pharmaceutical (Arcadia, Calif.) and methoxyflurane from Pitman-Moore Inc (Mundelein, Ill.). Sodium N,N-diethyldithiocarbamate (DETC), N-methyl-D-glucamine, and carbon disulfide were purchased from Aldrich (Milwaukee, Wis.). Pure .NO gas was purchased from Matheson (Joliet, Ill.), and pure argon gas was obtained from Airco (Murray Hill, N.J.). Saturated .NO solution in water was prepared by following the method of Kelm and Schrader (1). The concentration of the saturated .NO solution is 2.0 mM, as verified by an ISO-NO meter from World Precision Instruments (Sarasota, Fla.). $NO_2^-$ was measured by a colometric assay (2). $NO_3^-$ was first converted to $NO_2^-$ by E. coli nitrate reductase (3) and measured as described above. N-methyl-D-glucamine dithiocarbamate (MGD) was synthesized by following the method of Shinobu et al. (4).

EPR measurement

The EPR spectra were recorded with a home-built EPR spectrometer equipped with an S-band microwave bridge and a low-frequency loop-gap resonator with a 4-mm loop, operating at 3.5 GHz. Immediately after injection of the [$(MGD)_2$—$Fe^{2+}$] complex with or without SNP, the mouse housed in a plexiglass restraining tube was transferred to the S-band EPR spectrometer. The tail of the mouse was immobilized by tapping down with a thin and narrow plexiglass stick and then placed inside the resonator; no anesthetic agent was used. Microwave frequencies were measured by an EIP model 331 counter, and the magnetic field was calibrated with an MJ-110R Radiopan NMR magnetometer. Temperatures were monitored by a Fluke model 2100 digital thermometer. The field modulation amplitude was calibrated using Fremy salt as standard. Instrumental settings include 100-G scan range, 30-sec scan time, 0.1-sec time constant, 2.5-G modulation amplitude, 100-kHz modulation frequency and 25-mW microwave power.

Surgical preparation

All surgical procedures were approved by the Medical College of Wisconsin Animal Care Committee and the animals were closely monitored to insure that none experienced any undue stress or discomfort. The mice were anesthetized with sodium pentobarbital (50 mg/kg i.p.) and maintained at a stable depth of anesthesia with supplemental doses and/or (1%) methoxyflurane as required. They were placed on a heated surgical table and chronic indwelling catheters were inserted into the femoral artery and vein. All mice were fully awake and experiencing no apparent discomfort when they were returned to the Animal Resource Center.

Hemodynamic measurement

Measurements of blood pressure and heart rate were made on conscious mice from 1 to 14 days after surgery. The mice were trained to sit quietly in a plexiglass restraining tube for all blood pressure measurements. Blood pressure was measured using a solidstate pressure transducer (Cobe Laboratories, Lakewood, Colo.), and a general purpose amplifier. The data were collected at 200 Hz by microcomputer using data acquisition software (DATAQ Instruments Inc., Akron, Ohio).

Figure 1:
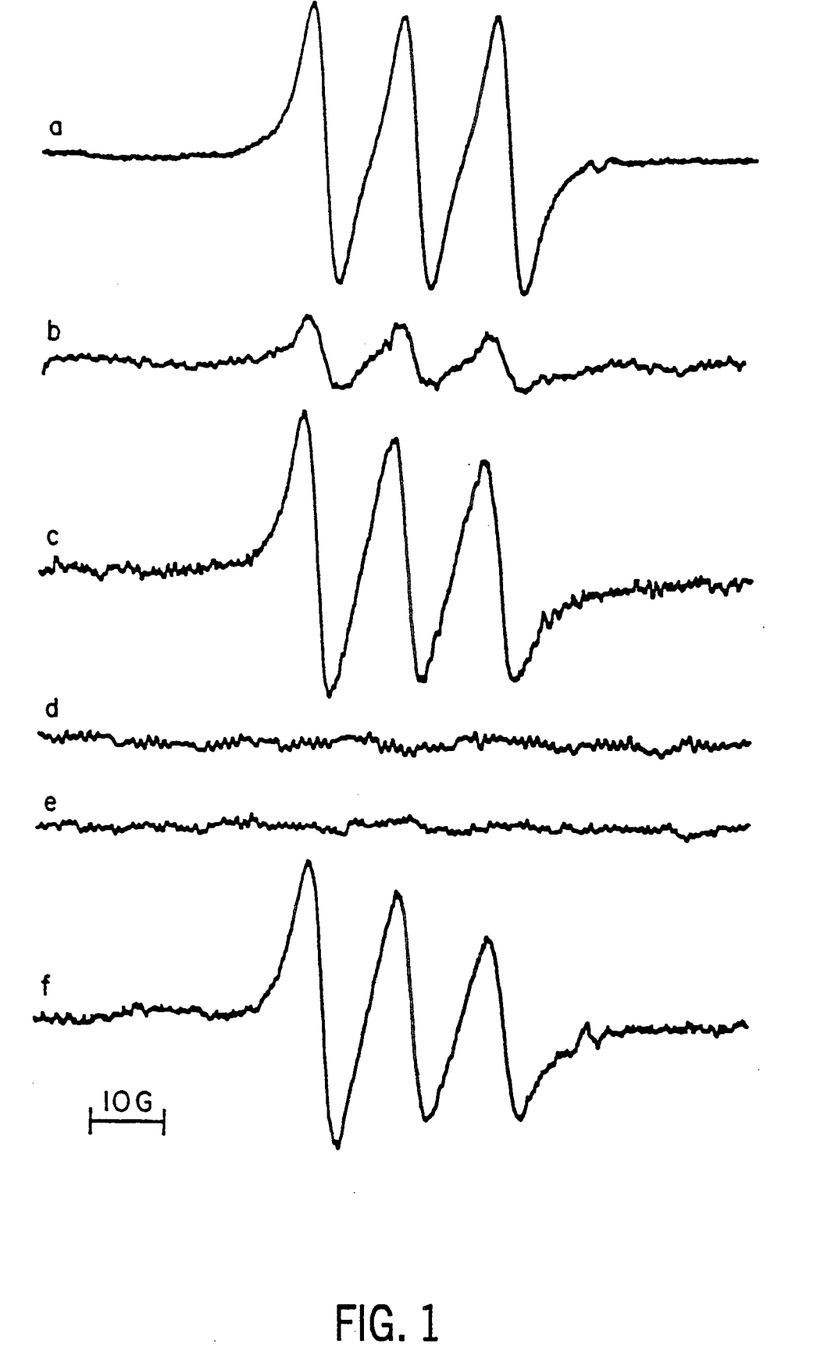
FIG. 1 shows the 3.5 GHz EPR spectra of the preferred complex [$(MGD)_2$—$Fe^{2+}$—NO] under various experimental conditions.

Addition of a small aliquot (55 μL) of saturated .NO solution to one mL of Tris-buffered solution containing MGD (75 mM) and $Fe^{2+}$ (15mM) at pH 7.4 gave rise to a three-line EPR spectrum ($a^N = 12.5$ G and $g_{iso} = 2.04$) at 22° C. (FIG. 1a), which is identified as the $[(MGD)_2—Fe^{2+}—NO]$ complex, similar to that of the $[(DETC)_2—Fe^{2+}—NO]$ complex reported previously by other investigators (5). This spin trapping of .NO can be performed in solution either in the presence or absence of oxygen. One interesting feature of the $[(MGD)_2—Fe^{2+}]$ complex is its high water-solubility, thus allowing the spin trapping of .NO in physiological conditions, either in vivo or in vitro. The $[(DETC)_2—Fe^{2+}]$ complex has been used to trap .NO in a variety of biological systems (5). However, because of its low water-solubility, DETC has to be incorporated into yeast membranes, which then served as carriers for the $[(DETC)_2—Fe^{2+}]$ complex.

When a 0.9% NaCl solution (0.1 mL) containing SNP (5 mg/kg) and the $[(MGD)_2—Fe^{2+}]$ complex was injected through the base of the lateral tail vein, an EPR signal was detected in the blood circulation of the mouse tail as shown in FIG. 1b. The spectral characteristics of FIG. 1b are identical to those of FIG. 1a, suggesting the in vivo spin trapping of .NO released from the metabolic activation of SNP to form the $[(MGD)_2—Fe^{2+}—NO]$ complex in the blood circulation. The concentration of the $[(MGD)_2—Fe^{2+}—NO]$ complex in FIG. 1b was about 10 μM. Injection of SNP at 20 mg/kg produced about four-fold increases in the signal intensity as shown in FIG. 1c as compared to that in FIG. 1b. The dose-dependent increase in the signal intensity suggests that the amount of the $[(MGD)_2—Fe^{2+}—NO]$ complex formed in vivo is proportional to the amount of .NO produced from SNP in the blood. In this latter experiment, mice were treated with α-ketoglutarate (0.5 g/kg) and sodium thiosulfate (1 g/kg) in 0.9% NaCl solution 15 minutes prior to SNP (20 mg/kg) injection to protect against the increase in blood cyanide levels induced by high SNP levels ($LD_{50}$ of 12 mg/kg in mice) as described by Yamamoto (6). Using this protection approach, we showed that SNP at doses of 20 mg/kg is well tolerated in mice. Injection of either SNP (20 mg/kg) alone (FIG. 1d) or the $[(MGD)_2—Fe^{2+}]$ complex alone (FIG. 1e) did not produce any detectable signal. Additionally, single or repeated injections of SNP or $[(MGD)_2—Fe^{2+}]$ complex or both are well tolerated with 100% survival without any observed adverse effects. Mice injected with a saline solution containing SNP (20 mg/kg) and the $[(MGD)_2—Fe^{2+}]$ complex were sacrificed and the heparin-treated whole blood was collected for EPR measurement. FIG. 1f showed that the EPR signal in the heparin-treated mouse whole blood is identical to that in FIG. 1b or 1c, a result suggesting that the EPR signal in FIG. 1b or 1c is due to the $[(MGD)_2—Fe^{2+}—NO]$ complex circulating in the blood rather than trapped in the tail muscle at or near the site of injection.

Figure 2:
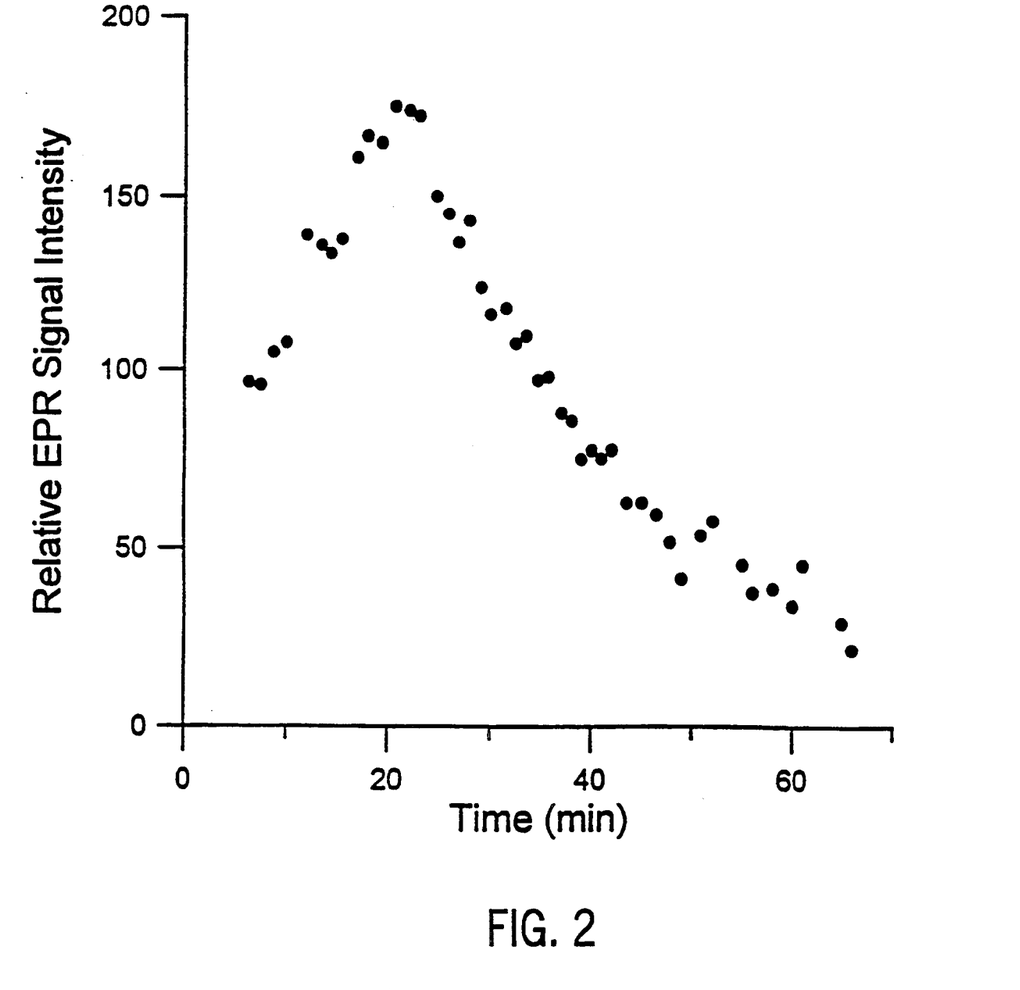
FIG. 2 shows the time course of the in vivo EPR signal intensities of the [$(MGD)_2$—$Fe^{2+}$—NO] complex in the blood circulation of the mouse tail.

The time course of the in vivo EPR signal of the $[(MGD)_2—Fe^{2+}—NO]$ complex in the blood circulation of the mouse tail is shown in FIG. 2. The mouse was injected with an aliquot (0.1 mL) of a mixture of SNP (20 mg/kg) and the $[(MGD)_2—Fe^{2+}]$ complex as described in FIG. 1c. Other experimental conditions were as described in FIG. 1.

The initial signal was shown to increase with time until it reached a maximum at 19±3 min and then decayed exponentially with a $t_½$ of about 15 min. This in vivo pharmacokinetics of the $[(MGD)_2—Fe^{2+}—NO]$ complex may be influenced by several factors including at least the rate of .NO production from SNP, and the rates of formation and decay of the $[(MGD)_2—Fe^{2+}—NO]$ complex. Assuming that the interaction between $[(MGD)_2—Fe^{2+}]$ and .NO is a fast process, and that the $[(MGD)_2—Fe^{2+}]$ complex is homogeneously distributed in the blood circulation, the observed initial increase in the EPR signal intensity may reflect mainly the rate of .NO release from SNP. The signal decay, on the other hand, is probably due to tissue distribution, biotransformation, and/or compartmentation of the $[(MGD)_2—Fe^{+2}—NO]$ complex. The exact mechanism is not yet known at present.

Figure 3:
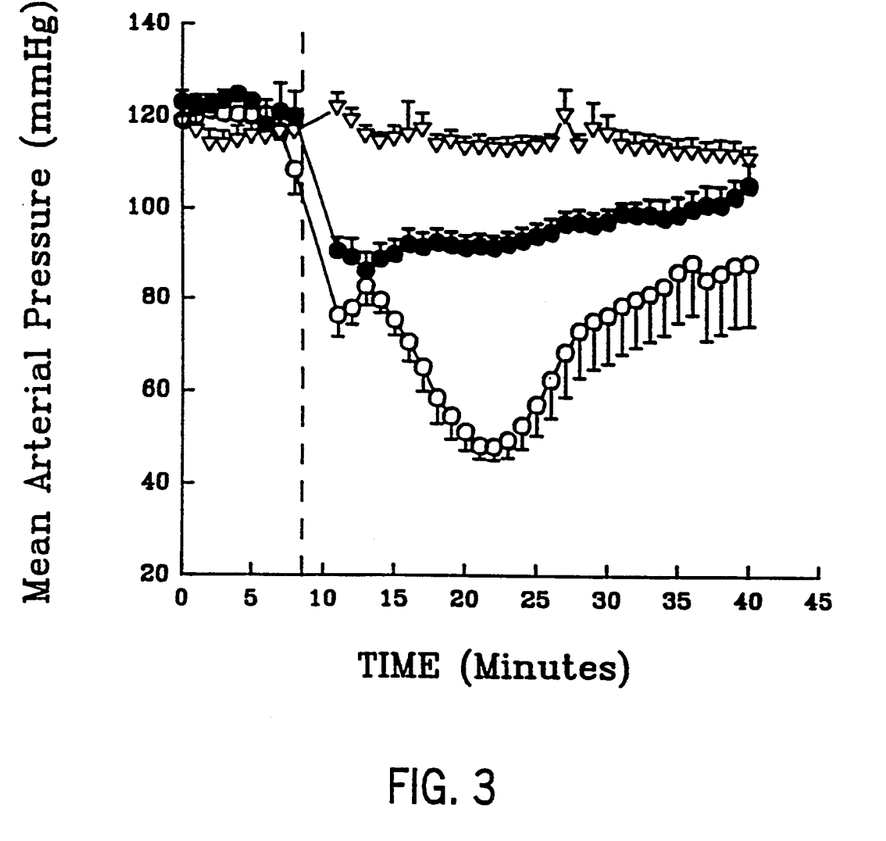
FIG. 3 shows the effects of sodium nitroprusside (SNP) and the [$(MGD)_2$—$Fe^{2+}$] complex on mean arterial pressure of mice.

In FIG. 3 the effects of SNP and the complex on the mean arterial pressure of mice is shown. An aliquot (0.1 mL) of a mixture of SNP and the $[(MGD)_2—Fe^{2+}]$ complex (●), SNP alone (○), or the $[(MGD)_2—Fe^{2+}]$ complex (▽) was injected intravenously through the femoral vein of catheterized mice. The final concentrations of MGD and $FeSO_4$ were 75 mM and 15 mM, respectively, and SNP dose was 5 mg/kg. Blood pressure was measured on conscious mice through an arterial catheter inserted in the femoral artery. The vertical broken line indicated the time at which various agents were infused intravenously.

As expected, the bolus infusion of SNP from the catheterized femoral vein resulted in a drastic drop in mean arterial pressure as measured from the catheterized femoral artery (FIG. 3, open circles). The mean arterial pressure returned to control levels about two hours following the SNP infusion. Interestingly, the infusion of SNP plus the $[(MGD)_2—Fe^{2+}]$ complex partially blocked the drop in mean arterial pressure (FIG. 3, closed circles). This argues that the in vivo trapping of .NO with the $[(MGD)_2—Fe^{2+}]$ complex to form the $[(MGD)_2—Fe^{2+}—NO]$ complex inhibits the vasodilating effect of SNP. This is in accordance with the contention that the vasodilating action of SNP is attributed to the release of .NO. The bolus infusion of the $[(MGD)_2—Fe^{2+}—NO]$ complex in saline solution (0.1 mM .NO concentration) did not produce any hemodynamic effects, indicating that the $[(MGD)_2Fe^{2+}—NO]$ complex is not an active form of .NO donor. In addition, the $[(MGD)_2—Fe^{2+}]$ complex alone also did not exert any effect on the mean arterial pressure (FIG. 3, open inverted triangles). The hemodynamic effects of SNP and the $[(MGD)_2—Fe^{2+}]$ complex in mice are summarized in Table I. It is worthy of noting that SNP reduces not only the mean arterial blood pressure, but also decreases the heart rate. The infusion of SNP and the $[(MGD)_2—Fe^{2+}]$ complex partially restored both the blood pressure and the heart rate.

TABLE I

Effects of SNP and [(MGD)$_2$-F$^{2+}$] Complex on Hemodynamic Properties in Mice

| Treatment | MAP[a] | SAP | DAP | HR |
|---|---|---|---|---|
| Control | 116 ± 3(5)[c] | 124 ± 6(5) | 105 ± 2(5) | 679 ± 21(5) |
| + [(MGD)$_2$-Fe$^{2+}$][b] | 113 ± 2(5) | 122 ± 5(5) | 104 ± 2(5) | 669 ± 18(5) |
| Control | 118 ± 2(5) | 130 ± 4(5) | 107 ± 4(5) | 700 ± 44(5) |
| + SNP | 46 ± 3(5)* | 57 ± 3(5)* | 40 ± 5(5)* | 472 ± 24(5)* |
| Control | 118 ± 5(5) | 133 ± 5(5) | 104 ± 8(5) | 692 ± 50(5) |
| + SNP + [(MGD)$_2$-Fe$^{2+}$] | 90 ± 3(5)*† | 101 ± 3(5)*† | 84 ± 3(5)*† | 635 ± 41(5)† |

[a]Abbreviations used: MAP, mean arterial pressure; SAP, systolic arterial pressure; DAP, diastolic arterial pressure; HR, heart rate.
[b]An aliquot (0.1 ml) of a mixture of SNP and the [(MGD)$_2$-Fe$^{2+}$] complex in saline solution was injected intravenously through the femoral vein. The final concentrations of MGD and FeSO$_4$ were 75 mM and 15 mM, respectively. SNP dose was 5 mg/kg.
[c]The data presented were taken 14 min after bolus infusion of agents, and were mean ± standard error (number of mice).
*p < 0.05 compared to control.
† p < 0.05 compared to the SNP-treated group.

The effects of infusion of SNP and the [(MGD)$_2$—Fe$^{2+}$] complex on NO$_2^-$ and NO$_3^-$ in the mouse blood are shown in Table II. Injection of SNP increased NO$_3^-$ levels in the blood due probably to the reaction of the released .NO with oxyhemoglobin to produce NO$_3^-$. Simultaneous infusion of SNP and the [(MGD)$_2$—Fe$^{2+}$] complex reduced NO$_3^-$ levels in the blood. The trapping of .NO with the [(MGD)$_2$—Fe$^{2+}$] complex therefore may at least partially block the .NO reaction with oxyhemoglobin, thus reducing NO$_3^-$ levels. No adverse effects of MGD or the (MGD)$_2$—Fe$^{2+}$ complex on mice were observed after intravenous infusion of these agents at doses of 0.3 mmoles/kg, which is consistent with the previous report by Shinobu et al. (4) in which they showed that MGD is not toxic to mice at doses of up to 8 mmoles/kg.

TABLE II

Effects of Sodium Nitroprusside and [(MGD)$_2$-Fe$^{2+}$] Complexes on Nitrite and Nitrate Concentrations in Mouse Sera

| | NO$_2$ (μM) | NO$_3^-$ (μM) | NO$_2^-$ + NO$_3^-$ (μM) |
|---|---|---|---|
| Control | 11.8 ± 2.2(6)[a] | 20.2 ± 3.4(6) | 32.1 ± 4.1(6) |
| + SNP | 12.3 ± 3.0(6) | 78.1 ± 8.7(6)* | 90.4 ± 10.3(6)* |
| + SNP + [(MGD)$_2$ — Fe$^{2+}$][b] | 21.9 ± 4.5(6) | 38.2 ± 5.4(6)*† | 60.1 ± 5.1(6)*† |

[a]The data presented were mean ± standard error (number of mice). Mice were sacrificed 15 min after bolus infusion of agents.
[b]SNP concentration was 5 mg/kg. The concentrations of MGD and FeSO$_4$ were 75 mM and 15 mM, respectively.
*p < 0.05 compared to control.
† p < 0.05 compared to the SNP-treated group.

Although the chemistry of SNP, a potent vasodilator, has been studied, some of its reaction mechanisms, particularly in the cell systems, are not very well characterized. Nevertheless, it is generally recognized that .NO is produced from SNP, only after one-electron reduction by cellular enzymes, thiols, or other reducing agents. On the basis of the rapid appearance of the [(MGD)$_2$—Fe$^{2+}$—NO] complex in the blood circulation upon simultaneous injection of the [(MGD)$_2$—Fe$^{2+}$] complex and SNP as shown in FIG. 2, it is safe to say that the in vivo one-electron reduction of SNP results in the release of .NO is a fast process. This may account for the immediate reduction of blood pressure in hypertensive patients upon i.v. administration of SNP.

EXAMPLE 2

In Vivo Spin-Trapping of Nitric Oxide in Septic-Shock Mice

Direct detection of nitric oxide (.NO) production in vivo in septic-shock mice was investigated by using the in vivo spin-trapping technique combined with electron paramagnetic resonance (EPR) spectroscopy. During the onset of septic shock, .NO was overproduced in mice via the arginine-nitric oxide synthase pathway.

Overproduction of nitric oxide, a potent endogenous vasodilator, has been implicated as the basis for hypotension and shock caused by endotoxin and the cytokines: tumor necrosis factor, interleukin-1 (IL-1), and IL-2.

Lipopolysaccharide (LPS) in saline (0.6 to 6 mg; E. coli 026:B6) was injected intravenously through the mouse tail vein. The mouse blood pressure was monitored through a catheterized femoral artery by a solid-state pressure transducer and a general purpose amplifier. The hypotensive effects of LPS administration were noted as the mean blood pressure dropped by 40 mmHg within 4 hours. The metal-chelator trapping reagent (MGD plus reduced iron) was injected subcutaneously or intravenously 2 hours prior to EPR measurement.

Figure 4:
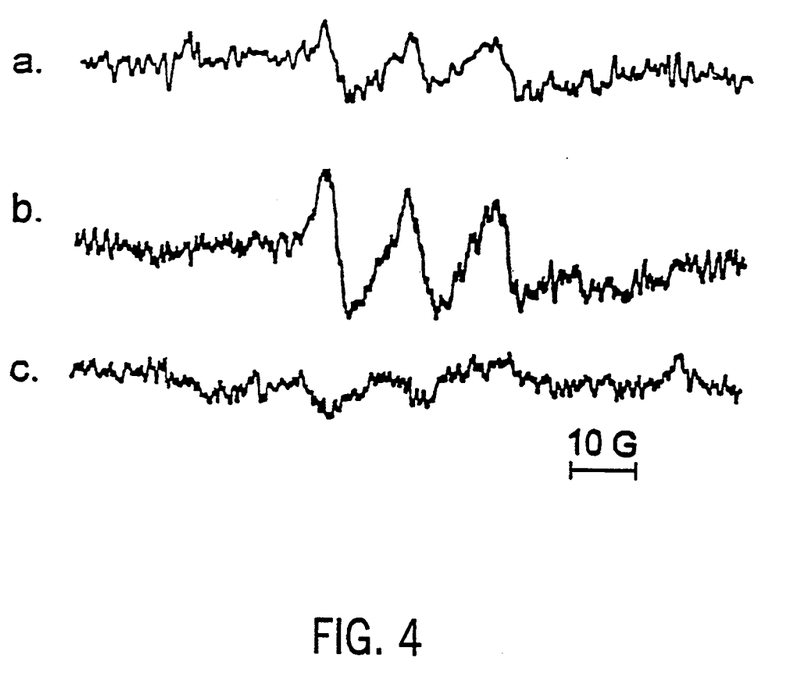
FIG. 4 shows the EPR spectra of the [$(MGD)_2$—$Fe^{2+}$—NO] complex formed in the blood circulation of the mouse tail.
Figure 5:
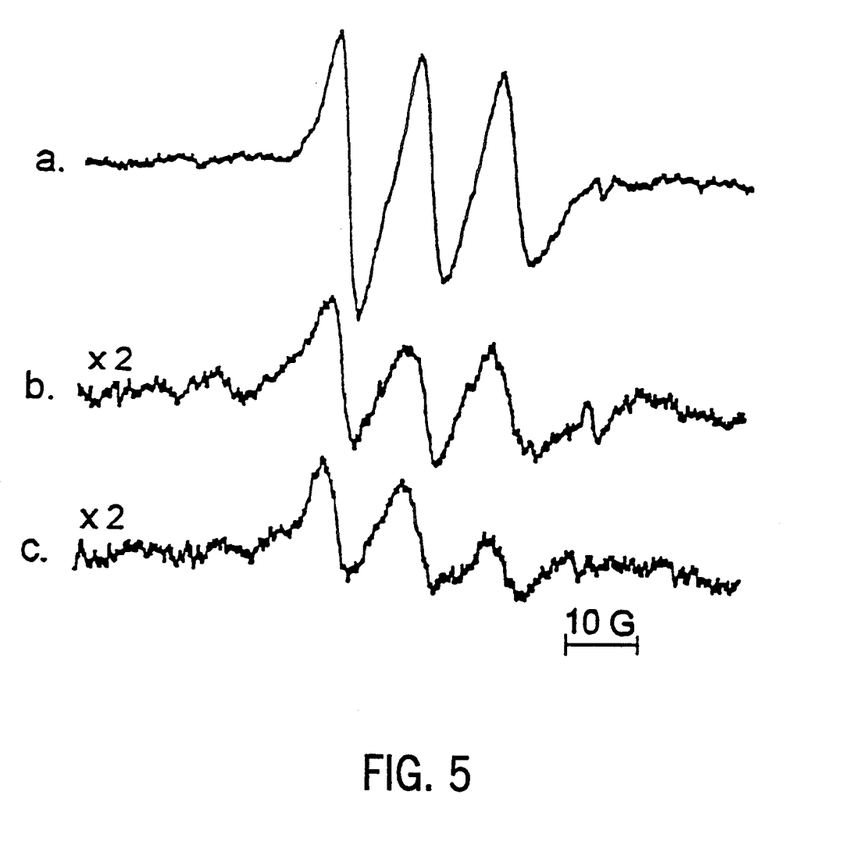
FIG. 5 shows the EPR spectra of the [$(MGD)_2$—$Fe^{2+}$—NO] complex in various tissues of the septic-shock mice.
Figure 6:
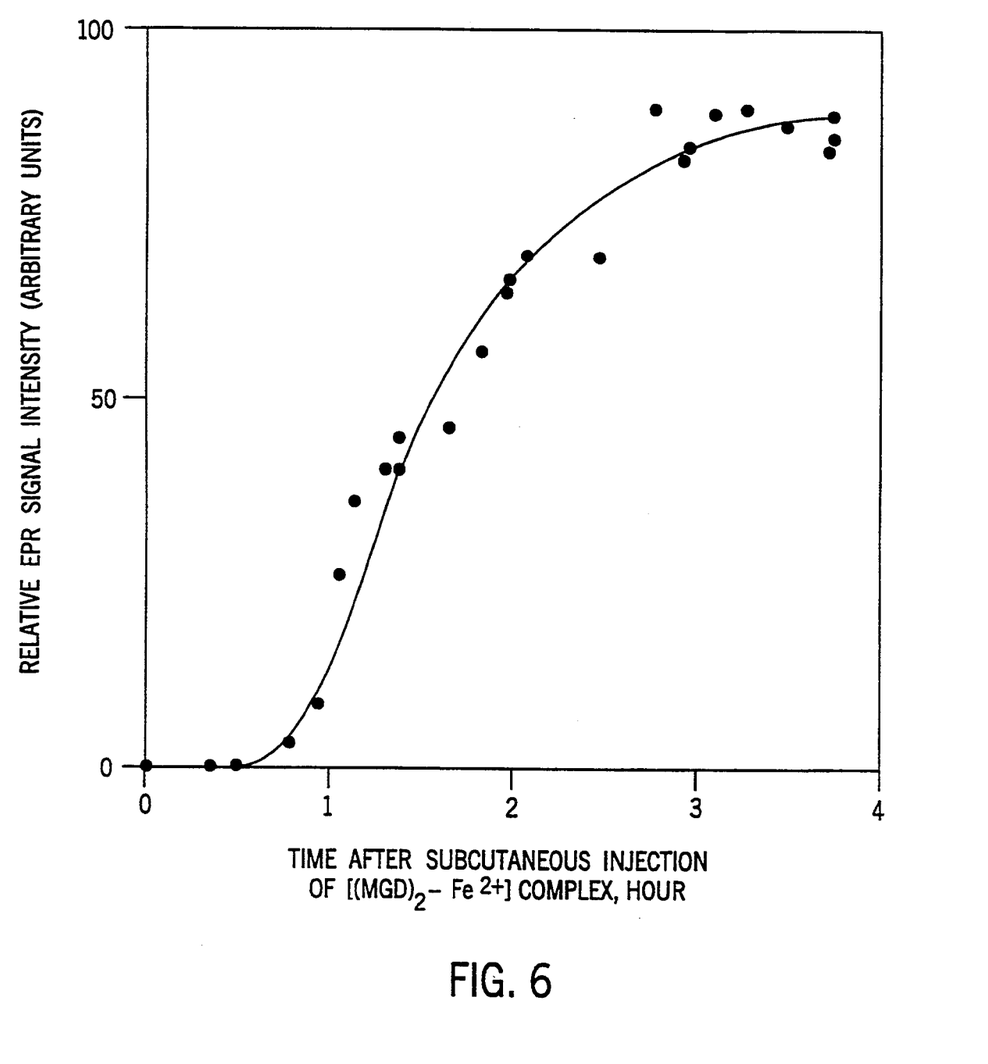
FIG. 6 shows the time course of the appearance of the in vivo EPR signal intensities of the [$(MGD)_2$—$Fe^{2+}$—NO] complex in the blood circulation of the septic-shock mice.
Figure 7:
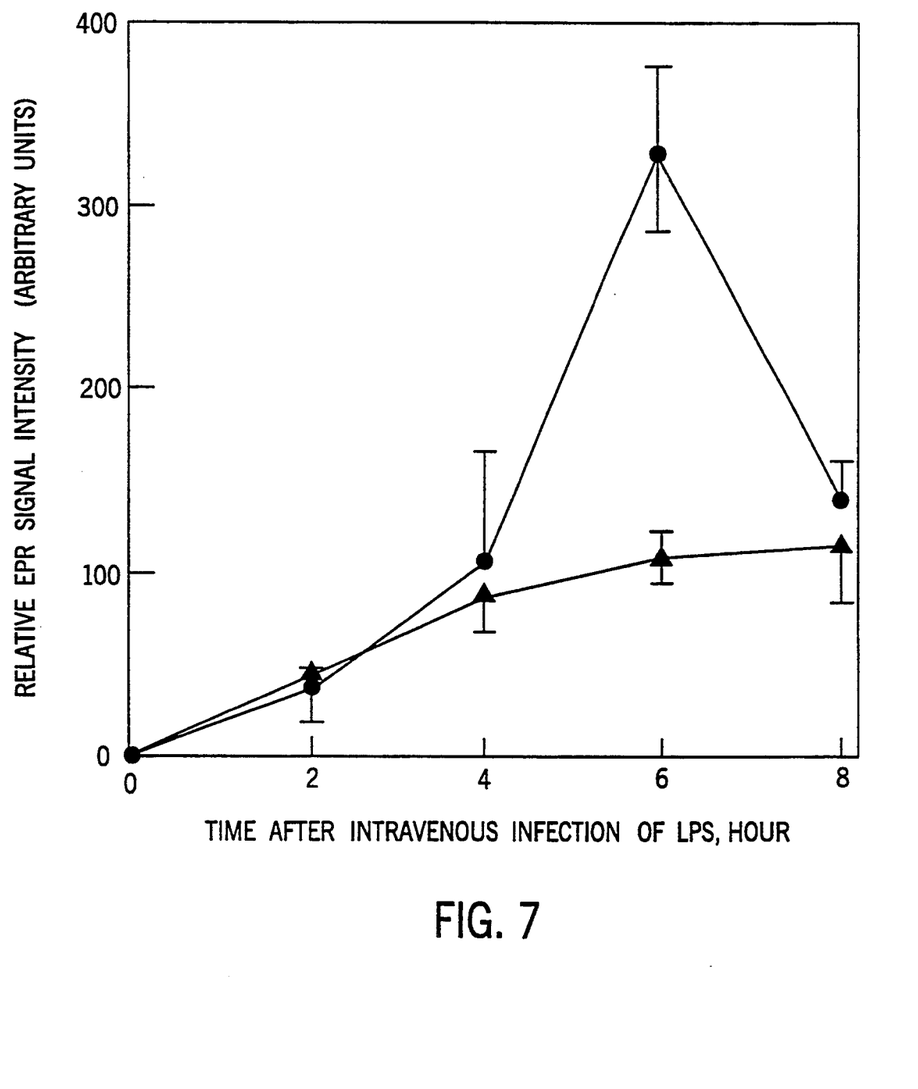
FIG. 7 shows the time course of the appearance of the EPR signal intensities of the [$(MGD)_2$—$Fe^{2+}$—NO] complex in isolated liver (●) and kidney (▲) tissues after intravenous injection of LPS.
Figure 8:
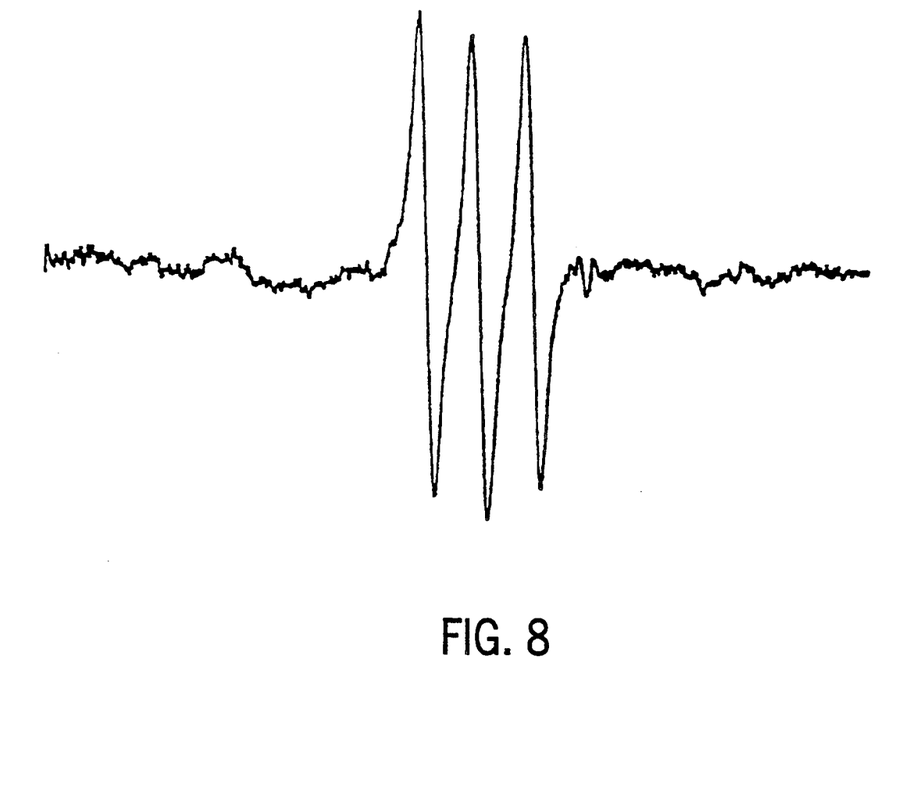
FIG. 8 shows the EPR spectrum of the [$(MGD)_2$—$Fe^{2+}$—NO] complex in the isolated urine of the septic-shock mice.

The results are seen in FIGS. 4–8:

In FIG. 4, there is shown the EPR spectra of the [(MGD)$_2$—Fe$^{2+}$—NO] complex formed in the blood circulation of the mouse tail four hours (FIG. 4a) and six hours (FIG. 4b) after LPS administration. This is the direct evidence of the overproduction of .NO in endotoxin-induced shock in living animals. FIG. 4c shows that the .NO production was inhibited by N$^G$-monomethyl-arginine (NMMA; 50 mg/kg), an inhibitor of .NO synthase, suggesting that the .NO detected was produced through the arginine-NO synthase pathway;

In FIG. 5, there is shown the EPR spectra of the $[(MGD)_2-Fe^{2+}-NO]$ complex in various tissues of the septic-shock mice. To determine the biodistribution of the $[(MGD)_2-Fe^{2+}-NO]$ complex formed in the septic-shock mice the animals were sacrificed and various tissues including liver, kidney and whole blood were transferred into capillary tubes for in vitro EPR measurement at 22° C. The results indicate the formation of the $[(MGD)_2-Fe^{2+}-NO]$ complex in liver kidney and whole blood as shown in FIG. 5a, 5b, and 5c, respectively;

In FIG. 6, there is shown the time course of the appearance of the in vivo EPR signal intensities of the $[(MGD)_2-Fe^{2+}NO]$ complex in the blood circulation of the septic-shock mouse;

In FIG. 7, there is shown the time course of the appearance of the EPR signal intensities of the $[(MGD)_2-Fe^{2+}-NO]$ complex in isolated liver (▲) and kidney (●) tissues after intravenous injection of LPS; and In FIG. 8, there is shown the EPR spectrum of the $[(MGD)_2-Fe^{2+}-NO]$ complex in the urine of the septic-shock mice.

As demonstrated in Example 2 the spin-trapping technique employing a water-soluble metal-chelator, such as a dithiocarbamate derivative chelated with reduced iron, combined with 3.5 GHz (S-band) EPR spectroscopy is suitable for studying in vivo .NO production in various physiological and pathophysiological conditions such as cytokine-mediated and septic shock. Using 9 GHz (X-band) or higher frequency EPR, where sample volume as little as a few microliters is needed, this spin-trapping technique also could be useful for measuring .NO production in cultured mammalian cells such as macrophages and endothelial cells.

In addition to the preferred metal-chelator other metal-chelators and chelating agents that form stable, water-soluble paramagnetic complexes with nitric oxide and metal ions already present in the body fluid (e.g. the iron of blood hemoglobin) can be used.

Similar results to those obtained with the preferred metal-chelator have been obtained with metal-chelators containing:
Iminodiacetic acid dithiocarbamate and its trisodium salt;
sarcosine dithiocarbamate and disodium salt;
di(hydroxyethyl)dithiocarbamate and its monosodium salt.

Representative of other chelating agents that may be used are the following:
N-benzyl-D-glucamine dithiocarbamate;
N-iso-amyl-N-glucamine dithiocarbamate;
N-(4-methylbenzyl)-D-glucamine dithiocarbamate;
Proline dithiocarbamate; and
N-p-isopropylbenzyl-D-glucamine dithiocarbamate.

The preferred metal for use in the metal-chelator is reduced iron ($Fe^{2+}$). However, other metal ions that are non-toxic to humans and other mammals under conditions of use and which form the desired complexes also can be used. Also as previously stated under some conditions it may be possible to simply inject a chelating agent into the bloodstream of the mammal and form to the complex with metal ions already present in the body fluid and nitric oxide.

It will be apparent to those skilled in the art that the method of detecting nitric oxide of the present invention also will be useful in the pharmaceutical industry for identifying drugs that could be useful in preventing or treating septic shock.

It also will be apparent to those skilled in the art that the examples have been for purposes of illustration and that modifications and changes can be made without departing from the scope of the invention. Therefore, it is intended that the invention be limited only by the claims.

REFERENCES

1. Kelm, M., and Schrader, J. (1990) Circ. Res., 66:1561–1575.
2. Green, L. C., Wagner, D. A., Glogowski, J., Skipper, P. L., Wishnok, J. S., and Tennenbaum, S. R. (1982) Anal. Biochem., 126:131–138.
3. Bartholomew, B. (1984) Fd. Chem. Toxic., 22:541–543.
4. Shinobu, L. A., Jones, S. G., and Jones, M. M. (1984) Acta Pharmacol, et Toxicol., 54:189–194.
5. Mordnintcev, P., Mulsch, A., Busse, R., and Vanin, A. (1991) Anal. Biochem., 199:142–146.
6. Yamamoto, H. A. (1992) Fd. Chem. Toxic., 30:887–890.

I claim:

1. A method for detecting nitric oxide in a body fluid of a mammal which comprises adding to said body fluid an effective amount of a chelating agent selected from the group consisting of
iminodiacetic acid dithiocarbamate and its trisodium salt;
sarcosine dithiocarbamate and its disodium salt; di(hydroxyethyl)dithiocarbamate and its monosodium salt;
N-methyl-D-glucamine dithiocarbamate;
N-benzyl-D-glucamine dithiocarbamate;
N-iso-amyl-N-glucamine dithiocarbamate;
N-(4-methylbenzyl)-D-glucamine dithiocarbamate;
proline dithiocarbamate; and
N-p-isopropylbenzyl-D-glucamine dithiocarbamate;
which will combine with any such amounts of nitric oxide and any metallic ions which act like reduced iron ions which may be present in the body fluid to form a water-soluble, paramagnetic complex and then detecting said complex by use of a magnetic resonance method at ambient temperature.

2. A method of claim 1 in which metallic ions also are added to the body fluid.

3. A method of claim 2 in which the metallic ions are reduced iron ($Fe^{2+}$).

4. A method of confirming that a mammal has septic shock which is characterized by the overproduction of nitric oxide in the body fluids of the animal, said method comprising adding to a body fluid of a mammal suspected of having septic shock, an effective amount of a chelating agent selected from the group consisting of
iminodiacetic acid dithiocarbamate and its trisodium salt;
sarcosine dithiocarbamate and its disodium salt;
di(hydroxyethyl)dithiocarbamate and its monosodium salt;
N-methyl-D-glucamine dithiocarbamate;
N-benzyl-D-glucamine dithiocarbamate;
N-iso-amyl-N-glucamine dithiocarbamate;
N-(4-methylbenzyl)-D-glucamine dithiocarbamate;
proline dithiocarbamate; and
N-p-isopropylbenzyl-D-glucamine dithiocarbamate;

and an effective amount of a nontoxic, iron ion to combine with any overproduced nitric oxide present in the body fluid to produce a water-soluble, stable paramagnetic complex of the chelating agent, nitric oxide and iron ions and then subjecting the body fluid to a magnetic resonance method which can detect the presence of such a water-soluble paramagnetic complex at ambient temperature.

5. The method of claim 4 in which the metallic ions are reduced iron ions.

6. A method of forming a water-soluble, paramagnetic complex in vivo with the nitric oxide overproduced in a body fluid of a mammal as a result of exposure to endotoxin, said method comprising introducing into said body fluid an effective amount of a chelating agent selected from the group consisting of iminodiacetic acid dithiocarbamate and its trisodium salt;
sarcosine dithiocarbamate and its disodium salt;
di(hydroxyethyl)dithiocarbamate and its monosodium salt;
N-methyl-D-glucamine dithiocarbamate;
N-benzyl-D-glucamine dithiocarbamate;
N-iso-amyl-N-glucamine dithiocarbamate;
N-(4-methylbenzyl)-D-glucamine dithiocarbamate;
proline dithiocarbamate; and
N-p-isopropylbenzyl-D-glucamine dithiocarbamate;

which combines with nitric oxide and reduced iron ions to form a water-soluble paramagnetic complex which can be detected by non-invasive methods.

* * * * *